United States Patent [19]

Zenitz

[11] 4,339,576
[45] Jul. 13, 1982

[54] ANTI-ASTHMATIC, ANTI-ALLERGIC, ANTI-CHOLINERGIC, BRONCHODILATOR AND ANTI-INFLAMMATORY 1-[(BENZOYLPHENYL)-LOWER-ALKYL]-PIPERIDINES AND ANALOGS THEREOF

[75] Inventor: Bernard L. Zenitz, Rensselaer, N.Y.

[73] Assignee: Sterling Drug Inc., New York, N.Y.

[21] Appl. No.: 295,759

[22] Filed: Aug. 24, 1981

Related U.S. Application Data

[60] Continuation-in-part of Ser. No. 261,881, May 8, 1981, abandoned, which is a division of Ser. No. 208,259, Nov. 19, 1980, Pat. No. 4,304,911.

[51] Int. Cl.$^3$ .................. C07D 211/26; C07D 211/34; C07D 413/04; C07D 413/06
[52] U.S. Cl. .................................... 544/130; 546/190; 546/191; 546/223; 546/224; 546/232; 546/234; 546/235
[58] Field of Search ................ 544/130; 546/223, 224, 546/234, 235, 190, 191, 232

[56] References Cited

FOREIGN PATENT DOCUMENTS 1549342 9/1967 France .
1508391 1/1976 United Kingdom .

Primary Examiner—Robert W. Ramsuer
Attorney, Agent, or Firm—William G. Webb; B. Woodrow Wyatt

[57] ABSTRACT

1-[(3- or 4-Benzoylphenyl)-lower-alkyl]-[(CH$_2$)$_n$—N=B]-substituted-piperidines, useful as anti-asthmatic, anti-allergic, anti-cholinergic, bronchodilator and anti-inflammatory agents, are prepared by alkylation of an appropriate substituted piperidine with a (3- or 4-benzoylphenyl)-lower-alkyl halide or tosylate; by reaction of a 1-[2-(3- or 4-lithiophenyl)-lower-alkyl]-[(CH$_2$)$_n$—N=B]-substituted-piperidine with benzonitrile and hydrolysis of the resulting benzimidoyl compound; or by reduction of a 1-[α-(3- or 4-benzoylphenyl)-lower-alkanoyl]-[(CH$_2$)$_n$—N=B]-substituted-piperidine. The analogous carbinols are prepared by reduction, with an alkali metal borohydride, of the ketone.

49 Claims, No Drawings

ANTI-ASTHMATIC, ANTI-ALLERGIC, ANTI-CHOLINERGIC, BRONCHODILATOR AND ANTI-INFLAMMATORY 1-[(BENZOYLPHENYL)-LOWER-ALKYL]PIPERIDINES AND ANALOGS THEREOF

RELATED APPLICATIONS

This is a continuation-in-part of my copending application Ser. No. 261,881, filed May 8, 1981 abandoned, which is a division of my copending application Ser. No. 208,259, filed Nov. 19, 1980 now U.S. Pat. No. 4,304,911.

BACKGROUND OF THE INVENTION (a) Field of the Invention

This invention relates to 1-[(3- or 4-benzoylphenyl)-lower-alkyl]-[$(CH_2)_n$—N=B]-substituted-piperidines and analogs thereof, useful as anti-asthmatic, anti-allergic, anti-cholinergic, bronchodilator and anti-inflammatory agents; to certain 1-[α-(3-or 4-benzoylphenyl)-lower-alkanoyl]-[$(CH_2)_n$—N=B]-substituted-piperidines, useful as intermediates for the preparation of the former, certain species of the former also being useful as analgesics and certain species of the latter being useful also as anti-inflammatory agents; and to certain 1-[(3- or 4-halophenyl)-lower-alkyl]-[$(CH_2)_n$—N=B]-substituted-piperidine which are also useful as intermediates for preparing the final products.

(b) Description of the Prior Art

British Pat. No. 1,508,391 discloses certain 1-[(3-benzoylphenyl)-lower-alkyl]piperidines, which are either unsubstituted in the piperidine ring or which are substituted by various hydrocarbon groups and which are disclosed as being useful as anti-inflammatory agents.

French Pat. No. 1,549,342, delivre Nov. 4, 1968, discloses certain 4-(benzoylphenylmethyl)morpholines useful as anti-inflammatory and anti-diabetic agents.

However, compounds of the 1-[(3- or 4-benzoylphenyl)-lower-alkyl]piperidine class substituted in the piperidine ring by basic, i.e. amine, functions are unknown. Moreover, the use of compounds of this general class as anti-asthmatics, anti-allergics, anti-cholinergics and bronchodilators likewise appears to be novel.

SUMMARY OF THE INVENTION

In a composition of matter aspect, this invention relates to certain 1-[2-(3- or 4-benzoylphenyl)-lower-alkyl]-[$(CH_2)_n$—N=B]-substituted-piperidines useful as anti-asthmatic, anti-allergic, anti-cholinergic, bronchodilator and anti-inflammatory agents, certain species of which are also useful as analgesics.

In another composition of matter aspect, the invention relates to particular species of 1-[1-(3-benzoylphenyl)-lower-alkyl]-[$(CH_2)_n$—N=B]-substituted piperidines, which are useful as anti-allergic, anti-cholinergic and anti-inflammatory agents.

In a further composition of matter aspect, the present invention relates to certain 1-[α-(3- or 4-benzoylphenyl)-lower-alkanoyl]-[$(CH_2)_2$—N=B]-substituted-piperidines, which are useful as intermediates for the preparation of the above-mentioned 1-[2-(3- or 4-benzoylphenyl)-lower-alkyl]-[$(CH_2)_n$—N=B]-substituted-piperidines, certain species of which are also useful as anti-inflammatory agents.

In a further composition of matter aspect, the invention relates to certain 1-[2-(3- or 4-halophenyl)-lower-alkyl]-[$(CH_2)_n$—N=B]-substituted-piperidines which are useful as intermediates for preparing the final products.

In a process aspect, the invention relates to a process for preparing the said 1-[2-(3- or 4-benzoylphenyl)-lower-alkyl]-[$(CH_2)_n$—N=B]-substituted-piperidines comprising reacting a 2-3- or 4-benzoylphenyl)-lower-alkyl tosylate with an appropriate [$(CH_2)_n$—N=B]-substituted-piperidine in the presence of an acid acceptor.

In a second process aspect, the invention relates to a process for preparing certain 1-[1-(3-benzoylphenyl)-lower-alkyl]-[$(CH_2)_n$—N=B]-substituted-piperidines comprising reacting a 1-(3-benzoylphenyl)-lower-alkyl halide with an appropriate [$(CH_2)_n$—N=B]-substituted-piperidine in the presence of an acid-acceptor.

In a third aspect, the invention relates to a process for preparing the said 1-[2-(3- or 4-benzoylphenyl)-lower-alkyl]-[$(CH_2)_n$—N=B]-substituted-piperidines which comprises reacting a 1-[2-(3- or 4-lithiophenyl)-lower-alkyl]-[$(CH_2)_n$—N=B]-substituted-piperidine with benzonitrile and hydrolyzing, in the presence of acid, the resulting 1-[2-(3- or 4-benzimidoylphenyl)-lower-alkyl]-[$(CH_2)_n$—N=B]-substituted-piperidine.

In a fourth process aspect, the present invention relates to a process for preparing the said 1-[2-(3-or 4-benzoylphenyl)-lower-alkyl]-[$(CH_2)_n$—N=B]-substituted-piperidines comprising reducing, with an alkali metal aluminum hydride, a ketal form of a corresponding 1-[α-(3-or 4-benzoylphenyl)-lower-alkanoyl]-[$(CH_2)_n$—N=B]-substituted-piperidine.

DETAILED DESCRIPTION INCLUSIVE OF THE PREFERRED EMBODIMENTS

More specifically this invention relates to 1-[2-(3- or 4-benzoylphenyl)-lower-alkyl]-[$(CH_2)_n$—N=B]-substituted-piperidines, which are useful as anti-asthmatic, anti-allergic, anti-cholinergic, bronchodilator and anti-inflammatory agents, having the formula

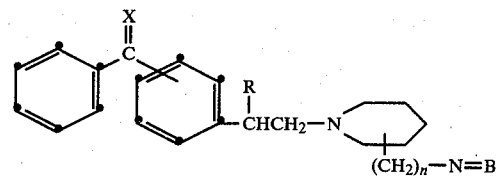

Ia where R is hydrogen or lower-alkyl; n is 0 or the integer 1; N=B is 1-piperidinyl, 4-morpholinyl, amino, di-loweralkylamino, lower-alkanoylamino, N-lower-alkyl-N-lower-alkanoylamino, cycloalkanecarbonylamino or benzoylamino, or benzoylamino substituted in the phenyl ring by loweralkyl, halogen (i.e. bromine, chlorine or fluorine) or lower-alkoxy; the group C=X is C=O or CHOH and where the Phenyl-C=X moiety of the [Phenyl-(C=X) Phenyl]—CHRCH$_2$ group is attached either to the 3- or the 4-position of the phenyl ring and the $(CH_2)_n$—N=B group is attached either to the 2-, 3- or 4-position of the piperidine ring.

Also within the purview of the invention are certain 1-[1-(3-benzoylphenyl)-lower-alkyl]-[C$_2$—N=B]-substituted-piperidines having the formula Ib:

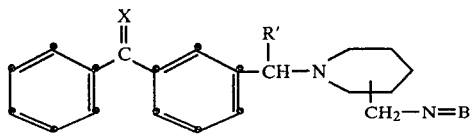

where R' is lower-alkyl; N=B is 1-piperidinyl or 4-morpholinyl; the group C=X has the same meanings given above; and the CH₂—N=B group is attached either to the 2-, 3- or 4-position of the piperidine ring.

As used herein the terms lower-alkyl, lower-alkoxy and lower-alkanoyl mean saturated, monovalent, aliphatic radicals, including branched chain radicals, of from one to six carbon atoms, for example, methyl, ethyl, propyl, isopropyl, butyl, hexyl, methoxy, ethoxy, propoxy, isopropoxy, formyl, acetyl, propionyl, α-methylpropionyl, hexanoyl and the like.

As used herein the term cycloalkane means saturated cyclic hydrocarbon rings containing from three to seven ring carbon atoms. The term is thus embracive of such groups, for example, as cyclopropyl, cyclobutyl, cyclopentyl, cyclohexyl and cycloheptyl.

The compounds of formula Ia where C=X represents C=O can be prepared by a variety of methods. One method comprises reacting a 2-(3- or 4-benzoylphenyl)-lower-alkyl tosylate of formula II with an appropriate [(CH₂)ₙ—N=B]-substituted-piperidine of formula III in the presence of an acid-acceptor according to the reaction:

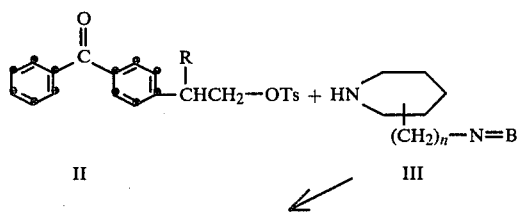

where R, n and N=B have the meanings given above, and Ts represents the p-toluenesulfonyl group. The reaction is preferably carried out by heating the reactants in an inert organic solvent, for example dimethylformamide (DMF), acetonitrile or a lower-alkanol. Suitable acid-acceptors are alkali metal carbonates or bicarbonates and an excess of the substituted-piperidine of formula III.

The tosylates of formula II are in turn prepared according to a sequence of reactions generally described in U.S. Pat. No. 4,216,326 which involves reduction, with an alkali metal borohydride, or a 3- or 4-bromophenyl-lower-alkanealdehyde or a 3- or 4-bromophenyl-lower-alkane carboxylic acid to the corresponding 3- or 4-bromophenyl-lower-alkanol; reaction of the latter with dihydropyran in the absence of solvent and in the presence of a strong acid; reaction of the resulting 3- or 4-bromophenyl-lower-alkyl tetrahydropyranyl ether with a lower-alkyl lithium followed by reaction of the resulting 3- or 4-lithiophenyl-lower-alkyl tetrahydropyranyl ether with benzonitrile and hydrolysis of the resulting 3- or 4- benzimidoylphenyl-lower-alkyl tetrahydropyranyl ether; and reaction of the resulting 3- or 4-benzoylphenyl-lower-alkanol with a p-toluenesulfonyl halide in the presence of pyridine.

The compounds of formula Ia where C=X is C=O can also be prepared by a sequence of reactions, also generally described in U.S. Pat. No. 4,216,326, involving reacting a 1-[2-(3- or 4-halophenyl)-lower-alkyl)]-[(CH₂)ₙ—N=B]-substituted-piperidine of formula IV below with a lower-alkyl lithium in an aprotic organic solvent, for example diethyl ether; reacting the resulting 1-[2-(3- or 4-lithiophenyl)-lower-alkyl]-[(CH₂)ₙ—N=B]-substituted-piperidine with benzonitrile; and hydrolyzing, with dilute mineral acid, the resulting 1-[2-(3- or 4-benzimidoylphenyl)-lower-alkyl]-[(CH₂)ₙ—N=B]-substituted-piperidine of formula V. The method is illustrated by the following reaction sequence:

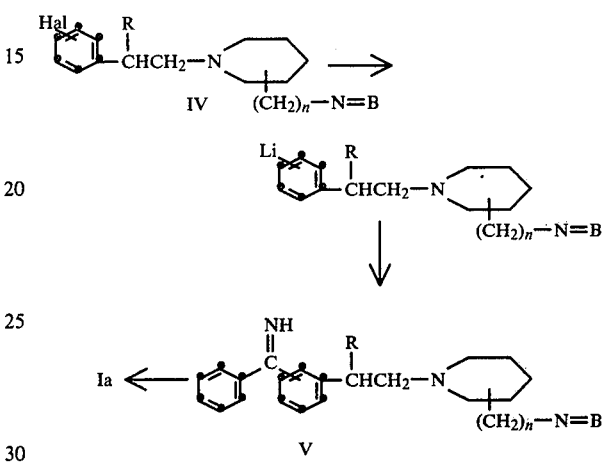

where R, n and N=B have the meanings given above, and Hal represents halogen.

The 1-[2- (3- or 4-halophenyl)-lower-alkyl]—[(CH₂)ₙ—N=B]-substituted-piperidines of formula IV are in turn prepared according to the general method described in U.S. Pat. No. 4,216,326 which comprises reacting a 2-(3- or 4-halophenyl)-lower-alkanal with an appropriate [(CH₂)ₙ—N=B]-substituted-piperidine; converting the resulting 1-[2-(3- or 4-halophenyl]-[(CH₂)ₙ—N=B]-substituted-piperidine to the iminium salt by reaction of the former with mineral acid; and reducing the iminium salt with an alkali metal borohydride or with hydrogen over a platinum oxide catalyst.

A further method for preparing the compounds of formula Ia comprises reducing, with an alkali metal aluminum hydride, a corresponding 1-[α-(3- or 4-benzoylphenyl)-lower-alkanoyl]-[(CH₂)ₙ—N=]-substituted-piperidine having the formula VI:

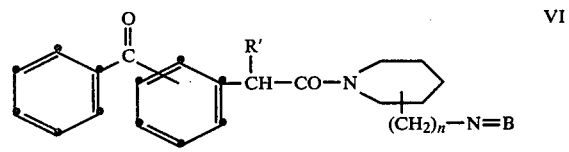

where R, n and N=B have the meanings given above. If it is desired to produce the compounds where C=X is C=O, the starting compounds of formula VI are first converted to a ketal form, for example the ethylene glycol ketal. The ketals are prepared by reaction of the ketone with an alcohol, for example ethylene glycol, in the presence of an acid catalyst under dehydrating conditions, and the ketal group is then removed by acid hydrolysis after reduction of the amide function. Otherwise, in the absence of such prior conversion to the ketal the compounds are reduced to the corresponding carbinols where C=X is CHOH.

The compounds of formula Ia where N=B is an amino group are prepared by hydrolysis, in the presence of an aqueous mineral acid, of a corresponding compound where N=B is lower-alkanoylamino. The reaction is carried out by heating a mixture of the reactants under reflux, the course of the reaction being followed by thin layer chromatography.

The compounds thus prepared can then be reacylated with a lower-alkanoyl halide, in order to prepare compounds where N=B is a different lower-alkanoylamino group, or with a cycloalkanecarbonyl halide or a benzoyl halide to prepare the compounds where N=B is, respectively, cycloalkanecarbonylamino or benzoylamino.

The compounds of formula Ib are prepared by reacting a 3-benzoylphenyl-CHR' halide of formula VII:

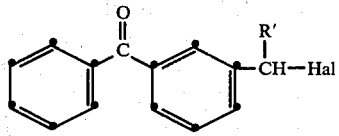

where R' and Hal have the meanings given above, with an appropriate (CH$_2$—N=B)-substituted-piperidine of formula III. The reaction is carried out in the presence of an acid-acceptor, for example an alkali metal carbonate or bicarbonate, in an inert organic solvent, for example, methanol, ethanol, isopropyl alcohol or dimethylformamide (DMF). If desired, an excess of the amine of formula III can serve as the acid-acceptor.

As noted before in the above described procedure for preparing the compounds of formula I by reduction of the amides of formula VI with an alkali metal aluminum hydride, when the ketone form of the compounds of formula VI is used as the starting material, the reduction also results in reduction of the carbonyl group to the carbinol function (C=X is CHOH). Moreover, reduction with an alkali metal aluminum hydride will also effect reduction of other carbonyl-containing functions, i.e. compounds where N=B is lower-alkanoylamino, N-lower-alkyl-N-lower-alkanoylamino, cycloalkanecarbonylamino or benzoylamino, or substituted benzoylamino. Therefore such reduction is not operative for reduction of the latter species. A preferred method for preparing all the compounds of formulas Ia/Ib where C=X is CHOH, and N=B has all the designated meanings comprises reduction of the corresponding compounds of formulas Ia/Ib where C=X is C=O with an alkali metal borohydride in an organic solvent inert under the conditions of the reaction, for example lower-alkanols, such as methanol, ethanol, or isopropanol, or DMF.

The novel compounds of the instant invention are the compounds of formulas Ia, Ib, IV and VI and the acid-addition salts thereof. The compounds of formulas Ia, Ib, IV and VI in free base form are converted to the acid-addition salt form by interaction of the base with an acid. In like manner, the free base can be regenerated from the acid-addition salt form in the conventional manner, that is by treating the salts with cold, weak aqueous bases, for example alkali metal carbonates and alkali metal bicarbonates. The bases thus regenerated can then be interacted with the same or a different acid to give back the same or different acid-addition salt.

Thus the novel bases and all of their acid-addition salts are readily interconvertible.

It will thus be appreciated that formulas Ia, Ib, IV and VI not only represent the structural configuration of the bases of formulas Ia, Ib, IV and VI but are also representative of the structural entities which are common to all of the compounds of formulas Ia, Ib, IV and VI, whether in the form of the free bases or in the form of the acid-addition salts of the bases. It has been found that, by virtue of these common structural entities, the bases and the acid addition salts of the compounds of formulas Ia, Ib and VI have inherent pharmacological activities of a type to be more fully described hereinbelow. These inherent pharmacological activities can be enjoyed in useful form for pharmaceutical purposes by employing the free bases themselves or the acid-addition salts formed from pharmaceutically-acceptable acids, that is acids whose anions are innocuous to the animal organism in effective doses of the salts so that beneficial properties inherent in the common structural entity represented by the free bases is not vitiated by side effects ascribable to the anions.

In utilizing the pharmacological activities of the salts of the invention, it is preferred, of course, to use pharmaceutically acceptable salts. Although water-insolubility, high toxicity, or lack of crystalline character may make some particular salt species unsuitable or less desirable for use as such in a given pharmaceutical application, the water-insoluble or toxic salts can be converted to the corresponding pharmaceutically-acceptable bases by decomposition of the salts with aqueous base as explained above, or alternatively they can be converted to any desired pharmaceutically-acceptable acid-addition salt by double decomposition reactions involving the anion, for example by ion-exchange procedures.

Moreover, apart from their usefulness in pharmaceutical applications, the salts are useful as characterizing or identifying derivatives of the free bases or in isolation or purification procedures. Like all of the acid-addition salts, such characterizing or purification salt derivatives can, if desired, be used to regenerate the pharmaceutically-acceptable free bases by reaction of the salts with aqueous base, or alternatively they can be converted to a pharmaceutically-acceptable acid-addition salt by, for example, ion-exchange procedures.

It will be appreciated from the foregoing that all of the acid-addition salts of the new bases are useful and valuable compounds, regardless of considerations of solubility, toxicity, physical form and the like, and are accordingly within the purview of the instant invention.

The novel feature of the compounds of the invention, then, resides in the concept of the bases and cationic forms of the new 1-[(3- or 4-benzoylphenyl)-lower-alkyl]-[(CH$_2$)$_n$—N=B]-substituted-piperidines and the carbinol analogs of formulas Ia and Ib and the new 1-[α-(3- and 4-benzoylphenyl)-lower-alkanoyl]-[(CH$_2$)$_n$—N=B]-substituted-piperidines of formula VI and not in any particular acid moiety or acid anion associated with the salt forms of the compounds; rather, the acid moieties or anions which can be associated with the salt forms are in themselves neither novel nor critical and therefore can be any acid anion or acid-like substance capable of salt formation with the bases. In fact, in aqueous solutions the base form or water-soluble acid-addition salt form of the compounds of the invention both possess a common protonated cation or ammonium ion.

Thus appropriate acid-addition salts are those derived from such diverse acids as formic acid, acetic acid, isobutyric acid, alpha-mercaptopropionic acid, malic acid, fumaric acid, succinic acid, succinamic acid, tartaric acid, citric acid, lactic acid, benzoic acid, 4-methoxybenzoic acid, phthalic acid, anthranilic acid, 1-naphthalenecarboxylic acid, cinnamic acid, cyclohexanecarboxylic acid, mandelic acid, tropic acid, crotonic acid, acetylenedicarboxylic acid, sorbic acid, 2-furancarboxylic acid, cholic acid, pyrenecarboxylic acid, 2-pyridinecarboxylic acid, 3-indoleacetic acid, quinic acid, sulfamic acid, methanesulfonic acid, isethionic acid, benzenesulfonic acid, p-toluenesulfonic acid, benzenesulfinic acid, butylarsonic acid, diethylphosphonic acid, p-aminophenylarsinic acid, phenylstibnic acid, phenylphosphinous acid, methylphosphinic acid, phenylphosphinic acid, hydrofluoric acid, hydrochloric acid, hydrobromic acid, hydriodic acid, perchloric acid, nitric acid, sulfuric acid, phosphoric acid, hydrocyanic acid, phosphotungstic acid, molybdic acid, phosphomolybdic acid, pyrophosphoric acid, arsenic acid, picric acid, picrolonic acid, barbituric acid, boron trifluoride, and the like.

The acid-addition salts are prepared by reacting the free base and the acid in an organic solvent and isolating the salt directly or by concentration of the solution.

Due to the presence of at least one and as many as two asymmetric centers in the compounds of the invention, i.e. the carbon atom adjacent the phenyl ring to which the R and R' groups are attached and the carbon atom of the piperidine ring to which the $(CH_2)_n$—N=B group is attached, the compounds of the invention can exist in stereochemically isomeric forms which are all considered to be within the purview of the invention. If desired, the isolation or the production of a particular stereochemical form can be accomplished by application of general principles known in the art.

In standard pharmacological test procedures, the compounds of formulas Ia and Ib, as well as certain species of compounds of formula VI, have been found to possess useful anti-inflammatory activity indicating utility of these compounds as anti-inflammatory agents. Certain species of formulas Ia and Ib have also been found to possess bronchodilator, anti-asthmatic, anti-allergic, anti-cholinergic and analgesic activities, indicating utility of these species as bronchodilators, anti-asthmatics, anti-allergics, anti-cholinergics and analgesics.

Anti-inflammatory activity was determined using (1) the inhibition of carrageenin-induced foot edema test described by Winter et al., Proc. Soc. Exp. Biol. and Med. 111, 554 (1962) as modified by Van Arman et al., J. Pharmacol. Exptl. Therap. 150, 328 (1965) and (2) a modification of the inhibition of adjuvant-induced arthritis test described by Pierson, J. Chronic Diseases 16, 863 (1963) and Glenn et al., Am. J. Vet. Res. 26, 1180 (1965).

The utility of the compounds of the invention as bronchodilators, anti-asthmatics, anti-allergics and anti-cholinergics was established by their effectiveness in standard pharmacological test proceecedures, for example the passive cutaneous anaphylaxis test in rats described by Mielens et al., Int. Arch. Allergy, 47, 633–649 (1974); a modified procedure of bronchoconstriction activity test in dogs described by Minatoya, J. Pharm. Exp. Therap., 206, 515–527 (1978); the anaphylactic bronchoconstriction activity test in guinea pigs, a modified procedure of Miller et al., Brit. J. Pharmacol, 58, 442P–443P (1976); the relaxation of guinea pig tracheal contractions by carbachol and by barium tests described by Spilker and Minatoya, Arch. int. de Pharmacodynamie et de Therap., 217, 201–217 (1975); and a modification of the human basophils test described by Magro, Immunochem., 12, 389 (1975) and by Conroy et al., Monogr. Allergy, 14, 307–309 (1979).

Bronchodilator activity was also determined using a test procedure baed on bronchoconstriction induced by histamine, acetylcholine and immune complex in guinea pigs which procedure is described as follows: guinea pigs of either sex, weighing 250–350 g. each, were fasted overnight, then anesthetized with 1.5 g. of urethane/kg. (i.p.) and the jugular vein and trachea were cannulated. The guinea pigs thus prepared were artificially respired with a rodent pump, and the intratracheal pressure was recorded continuously using a Statham transducer on a Grass polygraph. At five minute intervals, 5 $\mu$g./kg. of histamine phosphate (determined as base) was injected intravenously in order to ascertain that the maximum achievable bronchoconstrictor responsiveness (i.e. the increase in intratracheal pressure in mm. Hg) had been obtained, and the average of the last two increases in the intratracheal pressure was recorded. Acetylcholine was then injected intravenously at 15 $\mu$g./kg. five minutes after the last injection of histamine, and the increase in intratracheal pressure was again recorded. Two minutes following the injection of acetylcholine, 0.1 mg./kg. of propranolol was injected intravenously, and immune complexes [rabbit anti-bovine serum albumin (BSA) antibody/BSA complexes dissolved in excess BSA] were injected intravenously at 0.5 mg. of precipitating antibody/kg. three minutes following the injection of propanolol, and the increase in intratracheal pressure was again recorded.

Inhibition of bronchoconstriction was scored for each of the bronchoconstriction-inducers (i.e. histamine, acetylcholine and immune complex) with respect to the average bronchoconstriction in negative control guinea pigs (minimum of four guinea pigs in four days) according to the following criteria:

| % Inhibition | Score |
|---|---|
| 81–100 | 4 |
| 61–80 | 3 |
| 41–60 | 2 |
| 21–40 | 1 |
| 0–20 | 0 |

Test compounds scoring 3 or 4 against the three bronchoconstriction-inducers were considered active; those scoring 2 were considered marginally active; and those scoring 0 or 1 were considered marginally active; and those scoring 0 or 1 were considered inactive. Aminophylline, which was used as a reference drug, gave scores ranging from 3-3-2 to 4-4-3 for bronchoconstriction induced by histamine, acetylcholine and immune complex, respectively.

Generally speaking, the various bronchoconstrictor activity tests described above, i.e. the histamine induced bronchoconstriction activity test in dogs (Minatoya) and the histamine/acetylcholine/immune complex-induced bronchoconstriction test in guinea pigs, are used to define bronchodilator activity, while the passive cutaneous anaphylaxis test and the human basophils test can be used to define anti-allergic activity. Moreover, activity by test species against one of the types of bronchoconstriction in guinea pigs (induced by histamine, acetylcholine or immune complex) can indicate utility, respectively, as anti-histamines, anti-cholinergics or prostaglandin synthetase inhibitors. Species useful as anti-asthmatics ideally show both bronchodilator and anti-allergic parameters of activity, but species useful for such purpose can have either parameter alone without the other.

The test procedures used to determine the analgesic activity of the compounds have been described in detail in the prior art and are as follows: The acetylcholine-induced abdominal constriction test, which is a primary analgesic screening test designed to measure the ability of a test agent to suppress acetylcholine-induced abdominal constriction in mice, described by Collier et al., Brit. J. Pharmacol. Chemotherap. 32, 295 (1968); a modification of the anti-bradykinin test, which is also a primary analgesic screening procedure, described by Berkowitz et al., J. Pharmacol. Exp. Therap. 177, 500–508 (1971), Blane et al., J. Pharm. Pharmacol. 19, 367–373 (1967), Botha et al., Eur. J. Pharmacol. 6, 312–321 (1969) and Deffenu et al., J. Pharm. Pharmacol. 18, 135 (1966); the phenyl-p-quinone-induced writhing test, also a primary analgesic screening test, designed to measure the ability of a test agent to prevent phenyl-p-quinone-induced writhing in mice, described by Pearl and Harris, J. Pharmacol. Exptl. Therap. 154, 319–323 (1966); the rat tail flick radiant thermal heat analgesic (agonist) test described by D'Amour and Smith, J. Pharmacol. Exptl. Therap. 72, 74 (1941) as modified by Bass and VanderBrook, J. Am. Pharm. Assoc. Sci. Ed. 41, 569 (1956); and the phenazocine antagonist test, which is designed to measure the ability of a test agent to antagonize the effect of phenazocine in the above-indicated rat tail flick response test, described by Harris and Pierson, J. Pharmacol. Exptl. Therap. 143, 141 (1964).

The actual determination of the numerical pharmacological data for a particular compound of the invention is readily obtained according to the above-described standard test procedures by technicians versed in pharmacological test procedures without the need for any extensive experimentation.

In clinical practice, the compounds of formulas Ia, Ib and VI are normally administered orally or parenterally in a wide variety of dosage forms.

Solid compositions for oral administration include compressed tablets, pills, powders and granules. In such solid compositions, at least one of the active compounds is admixed with at least one inert diluent such as starch, calcium carbonate, sucrose or lactose. These compositions can also contain additional substances other than inert diluents, for example lubricating agents such as magnesium stearate, talc and the like.

Liquid compositions for oral administration include pharmaceutically-acceptable emulsions, solutions, suspensions, syrups and elixirs containing inert diluents commonly used in the art, such as water and liquid paraffin. Besides inert diluents, such compositions can also contain adjuvants, such as wetting and suspending agents, sweetening, flavoring, perfuming and preserving agents. According to this invention, the compounds for oral administration also include capsules of absorbable material such as gelatin containing the active component either with or without the addition of diluents or excipients.

Preparations according to the invention for parenteral administration include sterile aqueous, aqueous-organic and organic solutions, suspensions and emulsions. Examples of organic solvents or suspending media are propylene glycol, polyethylene glycol, vegetable oils such as olive oil and injectable organic esters such as ethyl oleate. The compositions can also contain adjuvants such as stabilizing, preserving, wetting, emulsifying and dispersing agents.

They can be sterilized, for example by filtration through a bacteria-retaining filter, by incorporation of sterilizing agents in the compositions, by irradiation or by heating. They can also be manufactured in the form of sterile solid compositions, which can be dissolved in sterile water or some other sterile injectable medium immediately before use.

The percentages of active component in such compositions may be varied so that a suitable dosage is obtained. The dosage administered to a particular patient is variable, depending upon the clinician's judgment using as criteria: the route of administration, the duration of treatment, the size and physical condition of the patient, the potency of the active component and the patient's response thereto. An effective dosage amount of the active component can thus only be determined by the clinician after a consideration of all criteria and utilizing his best judgment on the patient's behalf.

The structures of the compounds of the invention were established by the mode of synthesis, by elementary analyses and by ultraviolet, infrared and nuclear magnetic resonance spectra. The course of reactions and the homogeneity of the products were ascertained by thin layer chromatography.

The manner and process of making and using the invention, and the best mode contemplated by the inventor of carrying out the invention, will now be described so as to enable any person skilled in the art to which it pertains to make and use the same. The melting points are uncorrected.

Preparation of the Intermediates of Formulas II, III and IV

Preparation 1

A mixture of 98.4 g. (0.60 mole) of 2-chloromethylpyridine hydrochloride and 204.36 g. of piperidine in about 2 liters of benzene was refluxed with stirring for about sixteen hours, and the mixture was filtered after cooling to ambient temperature. The filter was washed with small portions of ether, and the combined filtrates were taken to dryness. Distillation of the residue in vacuo gave 105.4 g. of 2-(1-piperidinylmethyl)pyridine, b.p. 42°–63° C./0.04–0.09 mm., $n_D^{25} = 1.5240$.

The latter (34.9 g., 0.20 mole) was dissolved in 250 ml. of a solution of ethanol and 60 ml. of concentrated hydrochloric acid and reduced with hydrogen over 1.75 g. of platinum oxide at an initial pressure of 51 psig. When reduction was complete, the catalyst was removed by filtration, the filter was washed with ethanol, and the combined filtrates were taken to dryness to give a solid residue which was boiled with benzene and then collected and dried to give 51.6 g. of 2-(1-piperidinylmethyl)piperidine dihydrochloride, m.p. 228°–231° C.

Conversion of the latter (80.8 g.) to the free base by extracting the same into hexane from a strongly basified solution of the salt in water, and distillation of the product in vacuo afforded 53.9 g. of the free base, b.p. 45°–48° C./0.12–0.14 mm., $n_D^{25} = 1.4873$.

Following a procedure similar to that described in Preparation 1, the following compounds of formula III were similarly prepared:

Preparation 2

3-(1-Piperidinylmethyl)piperidine, b.p. 56°–57° C./(0.12 mm., $n_D^{25}=1.4924$), prepared by reaction of 98.4 g. (0.60 mole) of 3-chloromethylpyridine hydrochloride with 204.36 g. (2.4 moles) of piperidine in one liter of benzene and reduction of 29.4 g. of the resulting (101.4 g.) 3-(1-piperidinylmethyl)pyridine with hydrogen over 3.0 g. of platinum oxide in a solution of 250 ml. of ethanol and 50 ml. of concentrated hydrochloric acid to give 43.5 g. of the product in the form of the dihydrochloride salt (m.p. 259°–265° C.) followed by conversion of 100.8 g. of the latter to the free base.

Preparation 3

4-(1-Piperidinylmethyl)piperidine, b.p. 67°–68° C./0.35 mm, $n_D^{25}=1.4922$ (35.1 g.), prepared by reaction of 49.12 g. (0.3 mole) of 4-chloromethylpyridine hydrochloride with 102.18 g. (1.2 moles) of piperidine in 500 ml. of benzene; reduction of the resulting 49.38 g. of 4-(1-piperidinylmethyl)pyridine with hydrogen over 3.0 g. of platinum oxide in a solution of 250 ml. of ethanol and 75 ml. of concentrated hydrochloric acid to give 62.5 g. of the product in the form of the dihydrochloride salt (m.p. 265°–269° C.); and conversion of 59.6 g. of the latter to the free base.

Preparation 4

2-(4-Morpholinylmethyl)piperidine, b.p. 55°–59° C./0.03–0.15 mm., $n_D^{25}=1.4869$ (37.2 g.), prepared by reaction of 98.42 g. (0.06 mole) of 2-chloromethylpyridine hydrochloride with 210 g. (2.4 moles) of morpholine in one liter of acetonitrile; reduction of 17.82 g. (0.1 mole) of the resulting 98.08 g. of 2-(4-morpholinylmethyl)pyridine (b.p. 73°–76° C./0.20–0.25 mm., $n_D^{25}=1.5248$) with hydrogen over 1.0 g. of platinum oxide in a solution of 250 ml. of ethanol and 34.4 ml. of 6 N hydrochloric acid to give 16.89 g. of 2-(4-morpholinylmethyl)piperidine dihydrochloride, m.p. 256°–258° C.; and conversion of 64.5 g. of the latter to the free base.

Preparation 5

3-(4-Morpholinylmethyl)piperidine, b.p. 62°–64° C./0.15–0.20 mm., $n_D^{25}=1.4926$ (27.9 g.), prepared by reaction of 98.4 g. (0.6 mole) of 3-chloromethylpyridine hydrochloride with 210 g. (2.4 moles) of morpholine in 1200 ml. of acetonitrile to give 91.01 g. of 3-(4-morpholinylmethyl)pyridine, b.p. 78°–84° C./0.2–0.12 mm., $n_D^{30}$ 1.5264; reduction of 8.9 g. of the latter with hydrogen over 0.5 g. of platinum oxide in a solution of 250 ml. of ethanol and 17.2 ml. of 6 N hydrochloric acid to give 5.3 g. of 3-(4-morpholinylmethyl)piperidine dihydrochloride, m.p. 128°–146° C.; and conversion of 64.8 g. of the latter to the free base.

Preparation 6

4-(4-Morpholinylmethyl)piperidine, b.p. 59°–71° C./0.02–0.25 mm., $n_D^{25}=1.4918$ (50.9 g.), prepared by reaction of 98.42 g. (0.6 mole) of 4-chloromethylpyridine hydrochloride with 210 g. (2.4 moles) of morpholine in 1200 ml. of acetonitrile to give 83.99 g. of 4-(4-morpholinylmethyl)pyridine, b.p. 65.0°–74° C./0.01 mm., $n_D^{25}=1.5280$; reduction of 8.9 g. of the latter with hydrogen over 0.5 g. of platinum oxide in a solution of 250 ml. of ethanol and 17.2 ml. of 6 N hydrochloric acid to give 4.6 g. of 4-(4-morpholinylmethyl)pyridine dihydrochloride, m.p. 284°–286° C.; and conversion of 78 g. of the latter to the free base.

Preparation 7

A solution of 17.26 g. (0.1 mole) of 4-acetylaminopyridine hydrochloride in a solution of 200 ml. of absolute ethanol and 50 ml. of water was reduced with hydrogen over 2.0 g. of a 5% rhodium-on-charcoal catalyst under an initial hydrogen pressure of about 60 psig. When reduction was complete, the catalyst was removed by filtration, the filtrate was evaporated to dryness, and the residue was triturated with acetone, boiled with isopropyl alcohol, collected by filtration and dried to give 14.32 g. of 4-acetylaminopiperidine hydrochloride, m.p. 224°–226° C.

Preparation 8

A solution of 42.6 g. (0.2 mole) of 2-(3-bromophenyl)-propionaldehyde and 45 g. (0.25 mole) of 4-(1-piperidinylmethyl)piperidine in 500 ml. of benzene was heated under reflux under a Dean-Stark trap for about three hours, during which time 3.8 ml. of water were collected. The mixture was allowed to stand for about sixteen hours and then taken to dryness to give a residual oil which was distilled in vacuo in order to remove residual, unreacted 4-(1-piperidinylmethyl)piperidine The pot residue (77.2 g. of a yellow oil) was dissolved in hexane, the solution filtered, diluted with anhydrous ether, cooled and acidified with ethereal hydrogen chloride. The solid which separated was collected and dried to give 96 g. of 1-[2-(3-bromophenyl)propenyl]-4-(1-piperidinylmethyl)piperidine as the iminium chloride.

The latter (8 g., 0.18 mole) was suspended in 500 ml. of DMF, and the stirred mixture was treated in portions, while cooling to 2° C., with 13.6 g. (0.36 mole) of sodium borohydride. The mixture was stirred for an additional half hour in an ice bath, then for three hours at ambient temperature and decomposed by the addition of 200 ml. of 10% aqueous potassium hydroxide solution while stirring in an ice bath. The mixture was filtered to remove a white insoluble material, the filter was washed with hexane and ether, and the combined aqueous and hexane/ether washes were combined and shaken in a separatory funnel. The aqueous phase was separated and washed with two 200 ml. portions of hexane, and the combined organic extracts were extracted with 200 ml. of dilute hydrochloric acid. The acid extracts were washed with hexane and then basified by the addition of 100 ml. of 50% potassium hydroxide. The oil which separated was taken into hexane, and the combined hexane extracts, on evaporation to dryness, afforded 27.1 g. of an oil which was distilled in vacuo to give 16.3 g. of 1-[2-(3-bromophenyl)propyl]-4-(1-piperidinylmethyl)piperidine, b.p. 153°–159° C./0.03 mm, $n_D^{25}=1.5414$.

Following a procedure similar to that described in Preparation 8, the following compounds were similarly prepared:

Preparation 8A

1-[2-(3-Bromophenyl)propyl]-3-(1-piperidinylmethyl)piperidine dihydrochloride (5.2 g. from acetone) m.p. 168°–176° C., prepared by refluxing a solution of 42.6 g. (0.2 mole) of 2-(3-bromophenyl)propionaldehyde and 45 g. (0.25 mole) of 3-(1-piperidinylmethyl)- piperidine in 500 ml. of benzene under a Dean-Stark trap and reducing the resulting enamine hydrochloride with 15.1 g. (0.4 mole) of sodium borohydride in 250 ml. of DMF to give 6.3 g. of the product as the free base, b.p. 154°–159° C./0.1 mm.; $n_D25$ 1.5433, 5.9 g. of which were converted to the dihydrochloride in ethereal hydrochloric acid.

Preparation 8B

1-[2-(3-Bromophenyl)propyl]-2-(1-piperidinylmethyl)piperidine, b.p. 130°–138° C./0.03 mm., $n_D25$ 1.5410, prepared by refluxing a solution of 42.6 g. (0.2 mole) of 2-(3-bromophenyl)propionaldehyde and 45 g. (0.25 mole) of 2-(1-piperidinylmethyl)piperidine in 500 ml. of benzene under a Dean-Stark trap and reduction of the resulting enamine hydrochloride (94.3 g.) with 15.0 g. (0.4 mole) of sodium borohydride in 400 ml. of DMF and purification of the product by distillation in vacuo.

Preparation 9

To a stirred solution of 108.9 g. (0.51 mole) of α-(3-bromophenyl)propionaldehyde in one liter of absolute methanol was added, in portions, 38.8 g. (1.02 moles) of sodium borohydride while maintaining the temperature around 0° C. When addition was complete, the mixture was stirred at 3°–5° C. for one hour, then for four hours at ambient temperature and then treated, with stirring, with 125 ml. of acetone. Evaporation of the mixture to near dryness in vacuo afforded a heavy sludge of crystals and oil which was partitioned between 400 ml. of hexane and one liter of 10% potassium hydroxide. The organic phase was separated, the aqueous phase was further extracted with hexane, and the combined hexane extracts, after washing with brine, filtration and evaporation to dryness, afforded 105.7 g. of an oil which was distilled in vacuo to give 103.02 g. of 2-(3-bromophenyl)propanol, b.p. 74.5°–76.5° C./0.085–0.09 mm., $n_D^{25} = 1.5638$.

The latter (107.5 g., 0.5 mole) was mixed with 84.1 g. (1.0 mole) of dihydropyran, and the mixture was treated with 0.3 g. of anhydrous p-toluenesulfonic acid. An initial exothermic reaction set in, and when the temperature reached 65° C., the mixture was cooled in an ice bath. When the reaction had subsided, the excess dihydropyran was removed in vacuo, the mixture was cooled in an ice bath and treated with a few grams of anhydrous potassium carbonate and decanted from the undissolved p-toluenesulfonic acid. Dilution of the mixture with 250 ml. of hexane, filtration of the solution and removal of the solvent in vacuo afforded 152.2 g. of 2-(3-bromophenyl)propyl tetrahydropyranyl ether as a yellow oil.

A solution of the latter (152 g., 0.5 mole) in 250 ml. of ether was added over a five minute period to a mixture of 282 ml. (0.65 mole) of a 2.3 molar solution of butyl lithium in hexane while maintaining the temperature at −10° to −5° C. When addition was complete, the mixture was stirred at −10° C. for thirty minutes, then in an ice bath for two hours, and then treated, over a five minute period, with a solution of 73.1 g. (0.71 mole) of benzonitrile in 150 ml. of ether while maintaining the temperature at −10° to −5° C. The mixture was stirred at −10° C. for thirty minutes, then in an ice bath for two and one-half hours and allowed to stand at ambient temperature for about sixteen hours. The mixture was then treated cautiously with stirring with 300 ml. of 6 N hydrochloric acid, while allowing the ether to reflux during addition. The mixture was then heated under reflux for three hours, transferred to a separatory funnel, and the lower oily layer was separated, washed with three 200 ml. portions of water, and the aqueous washes added to the aqueous layer which was set aside. The ether layer from the reaction mixture was filtered, dried and evaporated to dryness to give 123.8 g. of a dark yellow oil. The aqueous layer was filtered to remove an insoluble viscous oil, and the aqueous filtrate was heated on a steam bath for an hour and a half. The oil which separated was taken into ether, the ether extracts were washed with saturated brine, then filtered, dried and evaporated to dryness to give 32.5 g. of a dark yellow oil which was combined with the 123.8 g. of oily material previously obtained. The combined oily fraction was dissolved in 300 ml. of ethanol, the solution was treated with 75 ml. of 6 N hydrochloric acid and the solution heated on the steam bath for an hour and a half. Evaporation of most of the solvent in vacuo afforded a residual oil which was partitioned between water and ether, and the aqueous layer was extracted with ether. The combined ether extracts, on washing with water, then with saturated sodium bicarbonate, filtration and evaporation to dryness afforded 128.5 g. of 2-(3-benzoylphenyl)propanol as an oil.

The latter (67.2 g., 0.28 mole) was dissolved in 300 ml. of pyridine and treated with a solution of 59.1 g. (0.31 mole) of p-toluenesulfonyl chloride in pyridine. The mixture was allowed to stand overnight, and the solid which separated was removed by filtration and the filtrate taken to dryness in vacuo. The last traces of pyridine were removed by distillation with 250 ml. portions of toluene, and the residue was filtered and the filter washed with toluene. The combined filtrates were diluted with 200 ml. of ether and the solution washed with dilute hydrochloric acid, then with saturated brine, then with saturated potassium carbonate, filtered, dried and taken to dryness to give 117.2 g. of an oily residue which was repeatedly boiled with dry hexane, the hexane being decanted off to give 81.6 g. of 2-(3-benzoylphenyl)propyl p-tosylate as a white crystalline solid, m.p. 53°–58° C.

Following a procedure similar to that described in Preparation 9, the following compounds of formula II were similarly prepared:

Preparation 10

2-(4-Benzoylphenyl)propyl p-tosylate (78.7 g.), m.p. 82°–84° C., prepared by reduction of 88.58 g. (0.42 mole) of α-(4-bromophenyl)propionaldehyde with 31.7 g. (0.84 mole) of sodium borohydride in 800 ml. of methanol to give 78.41 g. of 2-(4-bromophenyl)propanol, b.p. 79°–84.2° C./0.12–0.18 mm., $n_D^{25} = 1.5621$; reaction of 75.3 g. (0.35 mole) of the latter with 58.9 g. (0.7 mole) of dihydropyran in the presence of 0.3 g. of p-toluenesulfonic acid to give 108 g. of 2-(4-bromophenyl)propyl tetrahydropyranyl ether as a light brown oil; reaction of 107 g. (0.35 mole) of the latter with 214 ml. (0.45 mole) of a 2.1 molar solution of butyl lithium in hexane followed by reaction of the resulting lithio derivative with 51.5 g. (0.50 mole) of benzonitrile in anhydrous ether to give 56.6 g. of 2-(4-benzoylphenyl)propanol as a yellow viscous oil; (b.p. 163°–177° C./0.02–0.01 mole., $n_D^{23} = 1.5994$) and reaction of 56.0 g. (0.233 mole) of the latter with 47.7 g. (0.25 mole) of p-toluenesulfonyl chloride in 175 ml. of pyridine.

Preparation 11

2-(4-Benzoylphenyl)ethanol (40.12 g.), m.p. 78°–86° C., prepared by reaction of 130.69 g. (0.65 mole) of 2-(4-bromophenyl)ethanol with 109.2 g. (1.3 moles) of dihydropyran in the presence of a small amount of concentrated hydrochloric acid to give 189.63 g. of 2-(4-bromophenyl)ethanol tetrahydropyranyl ether; reaction of 85.5 g. (0.30 mole) of the latter with 178 ml. (0.39 mole) of a 2.18 molar solution of butyl lithium in anhydrous ether followed by reaction of the resulting lithio derivative with 40.26 g. (0.30 mole) of benzonitrile to give 43.64 g. of 2-(4-benzoylphenyl)ethanol, b.p. 201.0°–206.5° C./0.025–0.035 mm., $n_D^{23} = 1.6087$; and reaction of 29.4 g. (0.13 mole) of the latter with 29.4 g. (0.143 mole) of p-toluenesulfonyl chloride in 100 ml. of dry pyridine.

Preparation 12

A mixture of 9.95 g. (0.07 mole) of 4-acetylaminopiperidine, 12.7 g. (0.095 mole) of α-phenylpropionaldehyde and a trace of p-toluenesulfonic acid in 150 ml. of toluene was refluxed under a Dean-Stark trap for about one and a quarter hours, during which time 1.1 ml. of water was collected. The solution was then taken to dryness in vacuo, the residual traces of water were azeotroped by distillation with ethanol, and the residue was dissolved in 200 ml. of ethanol and the mixture reduced with hydrogen over platinum oxide under an initial hydrogen pressure of 42 psig. When reduction was complete, the catalyst was removed by filtration, the filtrate was taken to dryness, and the residue was partitioned between toluene/ethyl acetate and water. The layers were separated, and the organic extracts were washed with dilute hydrochloric acid. The combined aqueous phase was rendered strongly basic with aqueous potassium hydroxide and extracted two times with toluene. The toluene extracts, on washing with brine, drying over anhydrous sodium sulphate and evaporation to dryness, afforded 16.3 g. of an oil which was crystallized from toluene/hexane to give 12.95 g. of 1-(2-phenylpropyl)-4-acetylaminopiperidine, m.p. 102°–103° C.

Preparation 13

A mixture of 11 g. (0.03 mole) of 2-(3-bromophenyl)propyl p-tosylate, 5.5 g. (0.03 mole) of 4-(4-morpholinylmethyl)piperidine and 8.3 g. (0.06 mole) of anhydrous potassium carbonate in 100 ml. of anhydrous DMF was stirred and heated at 90° C. for about ten hours. An additional 1.1 g. of the tosylate was added, and the mixture was heated for an additional three hours. The mixture was then cooled to room temperature, filtered and the filtrate taken to dryness in vacuo. The residue was dissolved in diethy ether, the solution was washed three times with 500 ml. portions of water and then extracted with three 50 ml. portions of dilute hydrochloric acid. The combined acid extracts were basified with potassium carbonate solution, then extracted with three 100 ml. portions of diethyl ether, and the combined ether extracts were washed with brine, filtered and evaporated to dryness to give 9.9 g. of a pale yellow viscous oil which was distilled in vacuo, the portion boiling at 190°–193° C./0.03 mm. being collected as product. The material thus collected (7.6 g.) was dissolved in anhydrous diethyl ether, and the solution was acidified with ethereal hydrogen chloride. The material which separated was collected and recrystallized from ethanol/acetone to give 6.8 g. of 1-[2-(3-bromophenyl)propyl]-4-(4-morpholinylmethyl)piperidine dihydrochloride, m.p. 273°–276° C.

Preparation 14

Following a procedure similar to that described in Preparation 13 above, 1-[2-(3-bromophenyl)propyl]-2-(4-morpholinylmethyl)piperidine dihydrochloride (7.4 g.), m.p. 115°–140° C. (from anhydrous diethyl ether), was prepared by reaction of 12.1 g. (0.033 mole) of 2-(3-bromophenyl)propyl p-tosylate with 5.5 g. (0.03 mole) of 2-(4-morpholinylmethyl)piperidine in the presence of 8.3 g. (0.06 mole) of anhydrous potassium carbonate in 100 ml. of DMF and isolation of the product in the form of the dihydrochloride salt.

Preparation of the Intermediates of Formula VI

EXAMPLE 1A

To a stirred mixture of 10.17 g. (0.04 mole) of α-(3-benzoylphenyl)propionic acid in 25 ml. of benzene was added 9.52 g. (0.08 mole) of thionyl chloride, and the mixture was stirred and heated under reflux for three and a quarter hours. Evaporation of the mixture to dryness afforded an oil which was dissolved in 25 ml. of methylene dichloride and added to a solution of 4.86 g. (0.04 mole) of triethylamine and 7.29 g. (0.04 mole) of 4-(1-piperidinylmethyl)piperidine over a period of about fifteen to twenty minutes while maintaining the temperature at about 5° C. The mixture was stirred at ambient temperature for about three hours, washed first with water, then with sodium bicarbonate, and then with brine, filtered and taken to dryness to give 17.33 g. of 1-[α-(3-benzoylphenyl)propionyl]-4-(1-piperidinylmethyl)piperidine as a viscous oil.

A small amount of the latter was converted to the hydrochloride salt by addition of ethereal hydrogen chloride to an ether solution of the free base to give the hydrochloride salt, m.p. 211°–212° C.

Following a procedure similar to that described in Example 1A, the following compounds of formula VI were similarly prepared:

EXAMPLE 1B

1-[α-(3-Benzoylphenyl)propionyl]-2-(4-morpholinylmethyl)piperidine hydrochloride, m.p. 172°–203° C. (9.8 g. from acetone/diethyl ether), prepared by reacting 10.2 g. (0.04 mole) of α-(3-benzoylphenyl)propionic acid with 9.5 g. (0.08 mole) of thionyl chloride in 40 ml. of benzene and reaction of 8.2 g. (0.03 mole) of the resulting acid chloride with 5.4 g. (0.03 mole) of 2-(4-morpholinylmethyl)piperidine in the presence of 3.6 g. (0.03 mole) of triethylamine in 60 ml. of methylene dichloride.

EXAMPLE 1C

1-[α-(3-Benzoylphenyl)propionyl]-4-(4-morpholinylmethyl)piperidine hydrochloride, m.p. 221°–223° C. (10.5 g., from isopropyl alcohol/diethyl ether), prepared by reaction of 10.2 g. (0.04 mole) of α-(3-benzoylphenyl)propionic acid with 9.5 g. (0.08 mole) of thionyl chloride in 40 ml. of benzene and reaction of the resulting acid chloride with 5.4 g. (0.03 mole) of 4-(4-morpholinylmethyl)piperidine and 3.6 g. (0.036 mole) of triethylamine in 60 ml. of methylene dichloride.

EXAMPLE 1D

1-[α-(3-Benzoylphenyl)propionyl]-3-(4-morpholinylmethyl)piperidine hydrochloride, beige amorphous powder (10.6 g.), prepared by reaction of 16.5 g. (0.06 mole) of α-(3-benzoylphenyl)propionic acid with 15.5 g. (0.13 mole) of thionyl chloride in 80 ml. of benzene and reaction of 8.2 g. (0.03 mole) of the resulting acid chloride with 5.4 g. (0.03 mole) of 3-(4-morpholinylmethyl)piperidine and 3.6 g. (0.036 mole) of triethylamine in 60 ml. of methylene dichloride.

EXAMPLE 1E

1-[α-(3-Benzoylphenyl)propionyl]-2-(1-piperidinylmethyl)piperidine (9.9 g.) as a yellow viscous oil, prepared by reaction of 8.2 g. (0.03 mole) of α-(3-benzoylphenyl)propionyl chloride with 5.4 g. (0.03 mole) of 2-(1-piperidinylmethyl)piperidine and 3.6 g. (0.036 mole) of triethylamine in 60 ml. of methylene dichloride.

EXAMPLE 1F

1-[α-(3-Benzoylphenyl)propionyl]-3-(1-piperidinylmethyl)piperidine hydrochloride (10.1 g.) as an amorphous off-white powder, prepared by reaction of 8.2 g. (0.03 mole) of α-(3-benzoylphenyl)propionyl chloride with 5.4 g. (0.03 mole) of 3-(1-piperidinylmethyl)piperidine and 3.6 g. (0.036 mole) of triethylamine in 60 ml. of methylene dichloride.

Preparation of the Final Products of Formulas Ia/Ib

EXAMPLE 2

Following a procedure similar to that described in Preparation 9 above, 13.3 g. (0.035 mole) of 1-[2-(3-bromophenyl)propyl]4-(1-piperidinylmethyl)piperidine in 125 ml. of anhydrous diethyl ether was treated with 85 ml. (0.07 mole) of a 0.82 molar solution of butyl lithium in diethyl ether, and the resulting lithio derivative was treated with 7.9 g. (0.077 mole) of benzonitrile. After hydrolysis, with dilute acid, of the resulting 1-[2-(3-benzimidoylphenyl)propyl]-1-(1-piperidinylmethyl)piperidine, the product was isolated in the form of the hydrochloride salt which was recrystallized from ethanol/acetone to give 8.8 g. of 1-[2-(3-benzoylphenyl)propyl]-4-(1-piperidinylmethyl)piperidine dihydrochloride, m.p. 267°-270° C.

EXAMPLE 3A

A solution of 11.8 g. (0.03 mole) of 2-(3-benzoylphenyl)propyl p-tosylate and 12.8 g. (0.09 mole) of 4-acetylaminopiperidine in 200 ml. of acetonitrile was heated under reflux for eighty-eight hours and then taken to dryness in vacuo. The residue was partitioned between water and diethyl ether, and the ether layer was separated and washed first with water, then with brine, filtered and dried. The solution was then treated with an excess of ethereal hydrogen chloride, and the crystals which separated were collected and recrystallized from acetone/diethyl ether to give 8.3 g. of 1-[2-(3-benzoylphenyl)propyl]-4-acetylaminopiperidine hydrochloride, m.p. 108°-112° C.

Following a procedure similar to that described in Example 3A, the following compounds of formula Ia were similarly prepared:

EXAMPLE 3B

1-[2-(3-Benzoylphenyl)propyl]-4-(1-piperidinyl)piperidine dihydrochloride, m.p. 312°-314° C. (13.5 g. from ethanol), prepared by reaction of 11.7 g. (0.03 mole) of 2-(3-benzoylphenyl)propyl p-tosylate with 15.05 g. (0.09 mole) of 4-(1-piperidinyl)piperidine in 50 ml. of acetonitrile.

EXAMPLE 3C

1-[2-(4-Benzoylphenyl)propyl]-4-acetylaminopiperidine hydrochloride monohydrate, m.p. 128°-131° C. (9.5 g. from acetone/diethyl ether), prepared by reaction of 11.8 g. (0.03 mole) of 2-(4-benzoylphenyl)propyl p-tosylate with 12.8 g. (0.09 mole) of 4-acetylaminopiperidine in 300 ml. of acetonitrile.

EXAMPLE 3D

1-[2-(4-Benzoylphenyl)propyl]-4-(1-piperdinyl)piperidine dihydrochloride, m.p. 324°-325° C. (8.7 g. from methanol/ethanol, prepared by reaction of 9.9 g. (0.025 mole) of 2-(4-benzoylphenyl)propyl p-tosylate with 12.6 g. (0.075 mole) of 4-(1-piperidinyl)piperidine in 40 ml. of acetonitrile.

EXAMPLE 3E

1-[2-4-Benzoylphenyl)ethyl]-4-acetylaminopiperidine m.p. 145°-147° C. (21.6 g. from toluene), prepared by reaction of 30.4 g. (0.08 mole) of 2-(4-benzoylphenyl)ethyl p-tosylate with 17.0 g. (0.12 mole) of 4-acetylaminopiperidine in 350 ml. of acetonitrile in the presence of 22.1 g. (0.16 mole) of potassium carbonate.

EXAMPLE 3F

1-[2-(4-Benzoylphenyl)propyl]-4-dimethylaminopiperidine dihydrochloride, m.p. 293°-294° C. (6.8 g. from methanol/ethanol), prepared by reaction of 11.8 g. (0.03 mole) of 2-(4-benzoylphenyl)propyl p-tosylate with 5.1 g. (0.04 mole) of 4-dimethylaminopiperidine in 150 ml. of acetonitrile in the presence of 8.3 g. (0.06 mole) of potassium carbonate.

EXAMPLE 3G

1-[2-(4-Benzoylphenyl)propyl]-4-(N-acetyl-N-methylamino)piperidine hydrochloride, m.p. 240°-241° C. (7.4 g. from acetone), prepared by reaction of 11.8 g. (0.03 mole) of 2-(4-benzoylphenyl)propyl p-tosylate with 6.2 g. (0.04 mole) of 4-(N-acetyl-N-methylamino)piperidine in 150 ml. of acetonitrile in the presence of 8.3 g. (0.06 mole) of potassium carbonate.

EXAMPLE 4A

A mixture of 8.67 (0.03 mole) of 1-(3-benzoylphenyl)ethyl bromide, 6.08 g. (0.033 mole) of 4-(4-morpholinylmethyl)piperidine and 4.56 g. (0.033 mole) of potassium carbonate in 100 ml. of DMF was heated under reflux for four hours, and the mixture was then poured into 500 ml. of an ice/water mixture and the mixture extracted with hexane. The product crystallized from the hexane extracts as fine grains which were collected, dried and recrystallized from hexane to give 7.93 g. of 1-[1-(3-benzoylphenyl)ethyl]-4-(4-morpholinylmethyl)piperidine, m.p. 91.5-93.0.

Following a procedure similar to that described in Example 4A, the following compounds of formula Ib were similarly prepared.

EXAMPLE 4B

1-[1-(3-Benzoylphenyl)ethyl]-2-(4-morpholinylmethyl)piperidine dihydrochloride, m.p. 155°-165° C. (8.54 g. from acetone/diethyl ether), prepared by reaction of 11.56 g. (0.04 mole) of 1-(3-benzoylphenyl)ethyl bromide with 7.37 g. (0.04 mole) of 2-(4-morpholinylmethyl)piperidine in the presence of 6.08 g. (0.044 mole) of potassium carbonate in 100 ml. of DMF.

EXAMPLE 4C

1-[1-(3-Benzoylphenyl)ethyl]-3-(4-morpholinylmethyl)piperidine dihydrochloride monohydrate, m.p. 151°–168° C. (9.9 g. from diethyl ether), prepared by reaction of 11.56 g. (0.04 mole) of 1-(3-benzoylphenyl)ethyl bromide with 7.37 g. (0.04 mole) of 3-(4-morpholinylmethyl)piperidine in the presence of 6.08 g. (0.044 mole) of potassium carbonate in DMF.

EXAMPLE 4D

1-[1-(3-Benzoylphenyl)ethyl]-2-(1-piperidinylmethyl)piperidine dihydrochloride monohydrate, m.p. 141°–155° C. (11.1 g. from diethyl ether), prepared by reaction of 11.56 g. (0.04 mole) of 1-(3-benzoylphenyl)ethyl bromide with 7.29 g. (0.04 mole) of 2-(1-piperidinylmethyl)piperidine in the presence of 6.08 g. (0.044 mole) of potassium carbonate in 100 ml. of DMF.

EXAMPLE 4E

1-[1-(3-Benzoylphenyl)ethyl]-4-(1-piperidinylmethyl)piperidine dihydrochloride, m.p. 253°–255° C. (9.6 g. from ethanol/diethyl ether), prepared by reaction of 8.7 g. (0.03 mole) of 1-(3-benzoylphenyl)ethyl bromide with 5.47 g. (0.03 mole) of 4-(1-piperidinylmethyl)piperidine in the presence of 4.56 g. (0.033 mole of potassium carbonate in DMF.

EXAMPLE 5A

A solution of 16.9 g. (0.046 mole) of 1-[2-(4-benzoylphenyl)propyl]-4-acetylaminopiperidine in 100 ml. of 6 N hydrochloric acid was refluxed for twenty-six hours, and then taken to dryness in vacuo. The residue was azeotroped with ethanol to remove residual water, taken to dryness in vacuo, and then slurried with acetone and filtered. The residual solid was washed with diethyl ether and recrystallized from ethanol to give 12.9 g. of 1-[2-(4-benzoylphenyl)propyl]-4-aminopiperidine-dihydrochloride, m.p. 253°–255° C.

EXAMPLE 5B

Following a procedure similar to that described in Example 5A above, 1-[2-(4-benzoylphenyl)ethyl]-4-aminopiperidine dihydrochloride (4:3) hydrate, m.p. 260°–263° C. (15.4 g. from ethanol), was prepared by hydrolysis of 17 g. (0.049 mole) of 1-[2-(4-benzoylphenyl)ethyl]-4-acetylaminopiperidine in 90 ml. of 6 N hydrochloric acid.

EXAMPLE 6A

A stirred solution of 1-[2-(4-benzoylphenyl)propyl]-4-aminopiperidine dihydrochloride, 150 ml. of methylene dichloride and 10.5 g. (0.105 mole) of triethylamine was treated in portions with a solution of 3.9 g. (0.039 mole) of cyclopropanecarbonyl chloride in methylene dichloride. When addition was complete the mixture was allowed to stand at ambient temperature for twenty-four hours and then washed two times with water, once with aqueous potassium carbonate and once with brine and then dried and taken to dryness in vacuo. Recrystallization of the residue from diethyl ether gave 1-[2-(4-benzoylphenyl)propyl]-4-cyclopropanecarbonylaminopiperidine, m.p. 159°–160° C.

Following a procedure similar to that described in Example 6A, the following compounds of formula Ia were similarly prepared:

EXAMPLE 6B

1-[2-(4-Benzoylphenyl)propyl]-4-butyrylaminopiperidine, m.p. 107°–109° C. (8.8 g. from diethyl ether), prepared by reaction of 11.8 g. (0.03 mole) of 1-[2-(4-benzoylphenyl)propyl]-4-aminopiperidine dihydrochloride with 4.2 g. (0.039 mole) of butyryl chloride in the presence of 10.5 g. (0.105 mole) of triethylamine in 150 ml. of methylene dichloride.

EXAMPLE 6C

1-[2-(4-Benzoylphenyl)propyl]-4-benzoylaminopiperidine, m.p. 162°–163° C. (9.7 g. from diethyl ether), prepared by reacting 11.8 g. (0.03 mole) of 1-[2-(4-benzoylphenyl)propyl]-4-aminopiperidine dihydrochloride with 5.5 g. (0.039 mole). of benzoyl chloride in the presence of 10.6 g. (0.105 mole) of triethylamine in 150 ml. of methylene dichloride.

EXAMPLE 6D

1-[2-(4-Benzoylphenyl)propyl]-4-($\beta,\beta$-dimethylbutyrylamino)piperidine, m.p. 98°–99° C. (9.7 g. from diethyl ether), prepared by reaction of 11.8 g. (0.03 mole) of 1-[2-(4-benzoylphenyl)propyl]-4-aminopiperidine dihydrochloride with 4.4 g. (0.033 mole) of $\beta,\beta$-dimethylbutyryl chloride in the presence of 12.1 g. (0.12 mole) of triethylamine in 170 ml. of methylene dichloride.

EXAMPLE 6E

1-[2-(4-Benzoylphenyl)propyl]-4-propionylaminopiperidine, m.p. 105°–107° C. (6.1 g. from diethyl ether), prepared by reaction of 7.9 g. (0.02 mole) of 1-[2-(4-benzoylphenyl)propyl]-4-aminopiperidine dihydrochloride with 2.0 g. (0.022 mole) of propionyl chloride in the presence of 8.0 g. (0.08 mole) of triethylamine in 110 ml. of methylene dichloride.

EXAMPLE 6F

1-[2-(4-Benzoylphenyl)propyl]-4-cyclobutanecarbonylaminopiperidine, m.p. 145°–146° C. (6.2 g. from diethyl ether), prepared by reaction of 7.9 g. (0.02 mole) of 1-[2-(4-benzoylphenyl)propyl]-4-aminopiperidine with 2.6 g. (0.22 mole) of cyclobutanecarbonyl chloride in the presence of 7.0 g. (0.07 mole) of triethylamine in 110 ml. of methylene dichloride.

EXAMPLE 6G

1-[2-(4-Benzoylphenyl)propyl]-4-(4-methoxybenzoylamino)piperidine, m.p. 148°–149° C. (10.7 g. from ethyl acetate/diethyl ether), prepared by reaction of 11.8 g. (0.03 mole) of 1-[2-(4-benzoylphenyl)propyl]-4-aminopiperidine dihydrochloride with 5.6 g. (0.033 mole) of 4-methoxybenzoyl chloride in the presence of 10.6 g. (0.05 mole) of triethylamine in 150 ml. of methylene dichloride.

EXAMPLE 6H

1-[2-(4-Benzoylphenyl)propyl]-4-(4-bromobenzoylamino)piperidine, m.p. 158°–159° C. (6.6 g. from ethyl acetate/diethyl ether), prepared by reaction of 7.9 g. (0.02 mole) of 1-[2-(4-benzoylphenyl)propyl]-4-aminopiperidine dihydrochloride with 4.8 g. (0.022 mole) of 4-bromobenzoyl chloride in the presence of 7.1 g. (0.07 mole) of triethylamine in 125 ml. of methylene dichloride.

EXAMPLE 6I

1-[2-(4-Benzoylphenyl)propyl]-4-cyclohexanecarbonylaminopiperidine, m.p. 155°–156° C. (6.6 g. from acetone/diethyl ether), prepared by reaction of 7.9 g. (0.02 mole) of 1-[2-(4-benzoylphenyl)propyl]-4-aminopiperidine with 3.2 g. (0.022 mole) of cyclohexanecarbonyl chloride in the presence of 7.1 g. (0.07 mole) of triethylamine in 125 ml. of methylene dichloride.

EXAMPLE 7

To a stirred solution of 8.3 g. (0.023 mole) of 1-[2-(4-benzoylphenyl)propyl]-4-acetylaminopiperidine in 175 ml. of methanol was added 5.0 g. (0.18 mole) of sodium borohydride in portions over a twenty minute period while maintaining the reaction temperature at 0°–5° C. The mixture was stirred an additional two hours at 0°–5° C., treated with 25 ml. of acetone in order to destroy excess sodium borohydride and filtered. The filtrate was taken to dryness and the residue shaken with a mixture of 50 ml. of 10% aqueous potassium carbonate and a solution of 200 ml. of toluene and 100 ml. of diethyl ether. The organic layer was separated, washed first with 25 ml. of aqueous potassium carbonate, then with water, then with brine and then filtered. The filtrate was taken to dryness to give a colorless foam (7.7 g.) which, on trituration with anhydrous diethyl ether, afforded crystalline material which was collected and dried to give 6.1 g. of product. Recrystallization of the latter from toluene/diethyl ether afforded 5.8 g. of 1-[2-(α-hydroxy-4-benzylphenyl)propyl]-4-acetylaminopiperidine, m.p. 134°–135° C.

EXAMPLES 8A–8F

It is contemplated that, by conversion of the 1-[α-(3-benzoylphenyl)propionyl]-[(CH$_2$)$_n$-N=B]-substituted-piperidines described in Examples 1A–1F to their ethylene glycol ketals by heating a solution of the former in ethylene glycol under a Dean-Stark trap in the presence of a catalytic amount of p-toluenesulfonic acid, isolating the product under alkaline conditions, followed by reduction of the resulting ketal amides with lithium aluminum hydride in tetrahydrofuran, the product being isolated under acidic conditions, the following compounds of formula Ia can be prepared:

EXAMPLE 8A

1-[2-(3-benzoylphenyl)propyl]-4-(1-piperidinylmethyl)piperidine;

EXAMPLE 8B

1-[2-(3-benzoylphenyl)propyl]-2-(4-morpholinylmethyl)piperidine;

EXAMPLE 8C

1-[2-(3-benzoylphenyl)propyl]-4-(4-morpholinylmethyl)piperidine;

EXAMPLE 8D

1-[2-(3-benzoylphenyl)propyl]-3-(4-morpholinylmethyl)piperidine;

EXAMPLE 8E

1-[2-(3-benzoylphenyl)propyl]-2-(1-piperidinylmethyl)piperidine;

EXAMPLE 8F

1-[2-(3-benzoylphenyl)propyl]-3-(1-piperidinylmethyl)piperidine;

BIOLOGICAL TEST RESULTS

Utility of the 1-[(3- and 4-benzoylphenyl)-lower-alkyl]-[(CH$_2$)$_n$—N=B]-substituted-piperidines and their carbinol analogs of formulas Ia and Ib and the 1-[α-(3-benzoylphenyl)-lower-alkanoyl]-[(CH$_2$)$_n$—N=B]-substituted-piperidines of formula VI of the invention as anti-inflammatory agents was established by test results obtained in the carrageenin edema (CE) and adjuvant arthritis (AA) tests. Data so-obtained, stated in terms of percent inhibition at a dose expressed in terms of millimoles/kg., are given in TABLE A below. All data were obtained on oral administration in rats.

TABLE A

| Example | Dose | C.E. | A.A. |
|---|---|---|---|
| Compounds of Formula Ia | | | |
| 2 | .02 | — | 59** |
|  | .04 | — | 67** |
|  | .08 | 47** | 95** |
|  | .324 | 64** | 9 |
| 3A | .08 | 29** | 75** |
|  | .324 | 58**(2/8 dead) | — |
| 3B | .08 | 67** | — |
|  | .324 | 74**(⅛ dead) hypothermia 8/8 ataxic ⅛ | — |
| 3C | .08 | 41** | 19 |
|  | .324 | 53** | — |
| 3D | .08 | 42** | 86** |
|  | .324 | 46** | — |
| 6A | .08 | 72** | — |
|  | .324 | 77** | — |
| 6B | .04 | — | 38* |
|  | .08 | 54** | — |
|  | .324 | 63** | — |
| 6C | .08 | 50** | 51** |
|  | .324 | 57** | — |
| Compounds of Formula Ib | | | |
| 4A | .08 | 0 | — |
|  | .324 | 38* | — |
| 4B | .08 | 16 | — |
|  | .324 | 48**(convulsions 2/8 at 15 min.) | — |
| 4C | .08 | 0 | — |
|  | .324 | 55** | — |
| 4D | .08 | 27* | — |
|  | .324 | 59** | 56* |
| Compounds of Formula VI | | | |
| 1A | .08 | 14 | — |
|  | .324 | Toxic (6/8 dead) | — |
| 1B | .08 | 9 | 0 |
|  | .324 | 67** | — |
| 1C | .08 | 18 | 30 |
|  | .324 | 61** | — |
| 1D | .08 | 0 | 37 |
|  | .324 | 65** | — |
| 1E | .08 | 11 | — |
|  | .324 | 67** | — |
| 1F | .08 | 20 | — |
|  | .324 | Toxic (⅝ dead) | — |

Utility of the compounds of formulas Ia, Ib and VI as anti-asthmatics, anti-allergics, anti-cholinergics and bronchodilators was established by the test results obtained in the bronchoconstriction test in guinea pigs, where bronchoconstriction is induced by histamine, acetylcholine and immune complex (G. Pig); in the bronchoconstriction test in anesthetized dogs (Dog); in the in vitro histamine release from human basophils test (Hum. Bas.); and in the passive cutaneous anaphylaxis test (PCA). Data so-obtained are given in TABLE B below, the results in the guinea pig test being expressed in terms of inhibition scores at 100 mg./kg. (p.o.) described above; in the dog test in terms of the AED$_{40}$ (Approximate Effective Dose mg./kg. intraduodenally) resulting in 40% inhibition of bronchoconstriction; in the human basophils test in terms of AEC$_{50}$ (Approximate Effective Concentration) resulting in 50% inhibition of allergic release of histamine; and in the PCA test as a qualitative statement to indicate that the test species were considered active, weakly active or inactive.

TABLE B

| Example | G. Pig | Dog | Hum. Bas. | PCA |
|---|---|---|---|---|
| Compounds of Formula Ia | | | | |
| 2 | 0-0-4 | — | — | — |
| 3A | 3-0-4 | — | — | — |
| 3B | 0-0-4 | — | — | — |
| 3C | 4-4-3 | ~5.0 | >10$^{-5}$ | Inac. |
| 3D | 3-3-4 | Inac. | 9 × 10$^{-5}$ | Inac. |
| 5A | 0-2-3 | Inac. | — | — |
| 6A | 4-4-4 | 7.3 | Inac. | Weak |
| 6B | 4-2-4 | 2.0 | >10$^{-4}$ | Inac. |
| 6C | 4-0-4 | — | — | — |
| 6D | 1-0-3 | —. | — | — |
| 6E | 4-2-4 | 30 | — | — |
| Compounds of Formula Ib | | | | |
| 4A | 1-3-2 | >30 | — | — |
|  | 0-0-* | — | — | Actv. |
| Compounds of Formula VI | | | | |
| 1B | 0-0-2 | — | — | — |
| 1F | 0-1-* | — | — | Actv. |
| 1D | — | — | — | Actv. |

*Not tested

Utility of certain of the compounds of the invention as bronchodilators was also shown by test results obtained in the relaxation of guinea pig tracheal contractions by carbachol (Carb) and by barium (Ba) tests. The results, expressed in the carbachol test as the EC$_{50}$ (effective concentration in moles to produce 50% relaxation) and in the barium test as either active or inactive are given in Table C below.

TABLE C

| Example | Carb | Ba |
|---|---|---|
| 3G | 3.4 × 10$^{-7}$ | Inact. |
| 6I | 2.6 × 10$^{-6}$ | Active |
| 7 | 2.9 × 10$^{-6}$ | Slightly Active |

Utility of certain of the 1-[2-(3- and 4-benzoyl-phenyl)-lower-alkyl]-[(CH$_2$)$_n$—N=B]-substituted piperidines of formula Ia as analgesics was established by test results obtained in the acetylcholine-induced abdominal constriction test (Ach) and the anti-bradykinin test (BDK). Data so-obtained for the species found active in one or both of these tests are given in TABLE D below, results being expressed either in terms of the ED$_{50}$ or, in the acetylcholine-induced writhing test, as the percent inhibition of writhing in the test animals at a given dose level. The ED$_{50}$ is the calculated effective dose in 50% of the test animals. Data were obtained either on oral (p.o.) or subcutaneous (s.c.) administration as indicated.

TABLE D

| Example | Ach | BDK |
|---|---|---|
| 2 | 11 (s.c.) | 24 (p.o.) |
|  | 22 (p.o.) |  |
| 3A | 3.6 (p.o.) | 24 (p.o.) |
| 3B | 7.4 (p.o.) |  |
| 3C | 5.6 (p.o.) | 46 (p.o.) |

TABLE D-continued

| Example | Ach | BDK |
|---|---|---|
| 3D | 29 (p.o.) |  |
| 5A | 42 (p.o.) |  |
| 6A | 16 (p.o.) |  |
| 6B | 16 (p.o.) |  |
| 6C | 23 (p.o.) |  |

I claim:

1. A member of the group consisting of (A) a compound having the formula

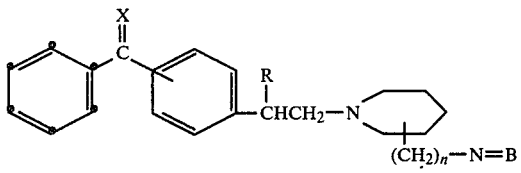

where R is hydrogen or lower-alkyl; n is O or the integer 1; N=B is 1-piperidinyl, 4-morpholinyl, amino, di-lower-alkylamino, lower-alkanoylamino, N-lower-alkyl-N-lower-alkanoylamino, cycloalkanecarbonylamino or benzoylamino, or benzoylamino substituted in the phenyl ring by lower-alkyl, halogen or lower-alkoxy; the group C=X represents C=O or CHOH and where the Phenyl-C=X moiety of the [Phenyl-(C=X)-Phenyl]-CHRCH$_2$ group is attached either to the 3-or 4-position of the phenyl ring; and the (CH$_2$)$_n$-N=B group is attached either to the 2-, 3- or 4-position of the piperidine ring; and (B) acid-addition salts thereof.

2. A compound according to claim 1 where C=X is C=O and the benzoyl group is attached to the 3-position of the phenyl ring.

3. A compound according to claim 1 where C=X is C=O and the benzoyl group is attached to the 4-position of the phenyl ring.

4. A compound according to claim 1 where C=X is CHOH and the Phenyl-CHOH group is attached to the 4-position of the phenyl ring.

5. A compound according to claim 2 where n is the integer 1.

6. A compound according to claim 2 where n is 0.

7. A compound according to claim 3 where n is the integer 1.

8. A compound according to claim 3 where n is 0.

9. A compound according to claim 4 where n is 0.

10. A compound according to claim 5 where N=B is 1-piperidinyl.

11. A compound according to claim 6 where N=B is 1-piperidinyl.

12. A compound according to claim 6 where N=B is lower-alkanoylamino.

13. A compound according to claim 8 where N=B is 1-piperidinyl.

14. A compound according to claim 8 where N=B is amino.

15. A compound according to claim 8 where N=B is lower-alkylamino.

16. A compound according to claim 8 where N=B is cycloalkanecarbonylamino.

17. A compound according to claim 8 where N=B is benzoylamino or substituted benzoylamino.

18. A compound according to claim 8 where N=B is di-lower-alkylamino.

19. A compound according to claim 8 where N=B is N-lower-alkyl-N-lower-alkanoylamino.

20. A compound according to claim 9 where N=B is lower-alkanoylamino.

21. 1-[2-(3-Benzoylphenyl)propyl]-4-(1-piperidinylmethyl)piperidine dihydrochloride according to claim 10.

22. 1-[2-(3-Benzoylphenyl)propyl]-4-(1-piperidinyl)piperidine dihydrochloride according to claim 11.

23. 1-[2-(3-Benzoylphenyl)propyl]-4-acetylaminopiperidine hydrochloride according to claim 12.

24. 1-[2-(4-Benzoylphenyl)propyl]-4-(1-piperidinyl)piperidine dihydrochloride according to claim 13.

25. 1-[2-(4-Benzoylphenyl)propyl]-4-aminopiperidine dihydrochloride according to claim 14.

26. 1-[2-(4-Benzoylphenyl)ethyl]-4-aminopiperidine dihydrochloride according to claim 14.

27. 1-[2-(4-Benzoylphenyl)propyl]-4-acetylaminopiperidine hydrochloride according to claim 15.

28. 1-[2-(4-Benzoylphenyl)ethyl]-4-acetylaminopiperidine according to claim 15.

29. 1-[2-(4-Benzoylphenyl)propyl]-4-butyrylaminopiperidine according to claim 15.

30. 1-[2-(4-Benzoylphenyl)propyl]-4-($\beta,\beta$-dimethylbutyrylamino)piperidine according to claim 15.

31. 1-[2-(4-Benzoylphenyl)propyl]-4-propionylaminopiperidine according to claim 15.

32. 1-[2-(4-Benzoylphenyl)propyl]-4-cyclopropanecarbonylaminopiperidine according to claim 16.

33. 1-[2-(4-Benzoylphenyl)propyl]-4-cyclobutanecarbonylaminopiperidine according to claim 16.

34. 1-[2-(4-Benzoylphenyl)propyl]-4-benzoylaminopiperidine according to claim 17.

35. 1-[2-(4-Benzoylphenyl)propyl]-4-(4-methoxybenzoylamino)piperidine according to claim 17.

36. 1-[2-(4-Benzoylphenyl)propyl]-4-(4-bromobenzoylamino)piperidine according to claim 17.

37. 1-2-(4-Benzoylphenyl)propyl]-4-cyclohexanecarbonylaminopiperidine according to claim 16.

38. 1-[2-(4-Benzoylphenyl)propyl]-4-dimethylaminopiperidine dihydrochloride according to claim 18.

39. 1-[2-(4-Benzoylphenyl)propyl]-4-(N-methyl-N-acetylamino)piperidine hydrochloride according to claim 19.

40. 1-{2-[4-($\alpha$-Hydroxybenzyl)phenyl]propyl}-4-acetylaminopiperidine according to claim 20.

41. A member of the group consisting of (A) compounds having the formula

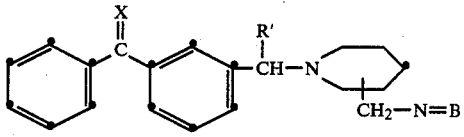

where R' is lower-alkyl; N=B is 1-piperidinyl or 4-morpholinyl; the group C=X represents C=O or CHOH, and the CH$_2$-N=B group is attached either to the 2-, 3- or 4-position of the piperidine ring; and (B) acid-addition salts thereof.

42. A compound according to claim 41 where the group C=X is C=O.

43. A compound according to claim 41 where N=B is 1-piperidinyl.

44. A compound according to claim 41 where N=B is 4-morpholinyl.

45. 1-[1-(3-Benzoylphenyl)ethyl]-2-(1-piperidinylmethyl)piperidine dihydrochloride according to claim 43.

46. 1-[1-(3-Benzoylphenyl)ethyl]-4-(1-piperidinylmethyl)piperidine dihydrochloride according to claim 43.

47. 1-[1-(3-Benzoylphenyl)ethyl]-4-(4-morpholinylmethyl)piperidine according to claim 44.

48. 1-[1-(3-Benzoylphenyl)ethyl]-2-(4-morpholinylmethyl)piperidine dihydrochloride according to claim 44.

49. 1-[1-(3-Benzoylphenyl)ethyl]-3-(4-morpholinylmethyl)piperidine dihydrochloride according to claim 44.

* * * * *

UNITED STATES PATENT AND TRADEMARK OFFICE
CERTIFICATE OF CORRECTION

PATENT NO. : 4,339,576
DATED : July 13, 1982
INVENTOR(S) : Bernard L. Zenitz

It is certified that error appears in the above-identified patent and that said Letters Patent are hereby corrected as shown below:

Column 3, line 52, change "or", first occurrence, to read --of--.

Column 4, lines 40 and 41, change "1-[2-(3- or 4-halophenyl-]-[(CH$_2$)$_n$ -N=B]..." to read --1-[2-(3- or 4-halophenyl)vinyl]-[(CH$_2$)$_n$ -N=B]...--.

Column 4, lines 50-58, in the structural formula change "R' " to read --R--.

Column 8, line 9, change "baed" to read --based--.

Column 18, line 22, change "1-[2-4-Benzoyl..." to read --1-[2-(4-Benzoyl...--.

Column 18, line 50, change "8.67" to read --8.67g.--.

Signed and Sealed this

Nineteenth Day of July 1983

[SEAL]

Attest:

GERALD J. MOSSINGHOFF

Attesting Officer     Commissioner of Patents and Trademarks